US010562834B2

(12) United States Patent
Berger et al.

(10) Patent No.: US 10,562,834 B2
(45) Date of Patent: Feb. 18, 2020

(54) PROCESS FOR PREPARING SUBSTITUTED CROTONIC ACIDS

(71) Applicant: Intervet Inc., Madison, NJ (US)

(72) Inventors: Michael Berger, Wiesbaden (DE); Stephan Veit, Budenheim (DE); Hans Peter Niedermann, Bubenheim (DE); Tobias Kappesser, Heidesheim (DE); Alfred Stutz, Zurich (CH)

(73) Assignee: Intervet Inc., Madison, NJ (US)

( * ) Notice: Subject to any disclaimer, the term of this patent is extended or adjusted under 35 U.S.C. 154(b) by 0 days.

(21) Appl. No.: 16/240,271

(22) Filed: Jan. 4, 2019

(65) Prior Publication Data

US 2019/0135725 A1    May 9, 2019

Related U.S. Application Data

(63) Continuation of application No. 15/312,013, filed as application No. PCT/EP2015/061038 on May 20, 2015.

(30) Foreign Application Priority Data

May 21, 2014   (EP) ..................................... 14169288

(51) Int. Cl.
| | |
|---|---|
| C07C 51/09 | (2006.01) |
| C07C 67/31 | (2006.01) |
| C07C 67/327 | (2006.01) |
| C07C 67/343 | (2006.01) |
| C07C 67/30 | (2006.01) |
| C07C 67/313 | (2006.01) |

(52) U.S. Cl.
CPC .............. *C07C 51/09* (2013.01); *C07C 67/30* (2013.01); *C07C 67/31* (2013.01); *C07C 67/313* (2013.01); *C07C 67/327* (2013.01); *C07C 67/343* (2013.01)

(58) Field of Classification Search
CPC ......... C07C 51/09; C07C 67/30; C07C 67/31; C07C 67/313; C07C 67/327; C07C 67/343
USPC ....................................................... 562/599
See application file for complete search history.

(56) References Cited

FOREIGN PATENT DOCUMENTS

| WO | 2011138250 A1 | 11/2011 |
| WO | 2012041872 A1 | 4/2012 |
| WO | 2012041873 A1 | 4/2012 |
| WO | 2013144179 A1 | 10/2013 |
| WO | 2013144180 A1 | 10/2013 |

OTHER PUBLICATIONS

Taber F et al: "Enantioselective Construction of Cyclic Quaternary Centers: (-)-Mesennbrine", The Journal of Organic Chemistry, American Chemical Society, US, vol. 66, Jan. 1, 2001 (Jan. 1, 2001 ), pp. 143-147.*

Borner et al: "Copper-Catalysed Asymmetric 1,4-Addition of Organozinc Compounds to Linear Aliphatic Enones Using 2,2' Dihydroxy 3,3'-Dithioether Derivatives of 1, 1 '-Binaphthalene", European Journal of Organic Chemistry,vol. 2001, No. 13, Jun. 5, 2001 (Jun. 5, 2001), pp. 2435-2446.*

Yamazaki T et al: "Stereoselective preparation of ethyl 2,3-dihydroxy-4,4,4-trifluorobutyrates via enzymatic optical resolution", Tetrahedron Asymmetry, Pergamon Press Ltd, Oxford, GB,vol. 1, No. 8, Jan. 1, 1990 (Jan. 1, 1990 ), pp. 521-524.*

Tamura Ket Al: "The effect of fluoromethyl groups on the diastereoselectivity in the electrophilic alkylation", Journal of Fluorine Chemistry, Elsevier, NL, vol. 126, No. 6, Jun. 1, 2005 (Jun. 1, 2005 ), pp. 918-930.*

Jagodzinska et al: "Studies on a three-step preparation of betafluoroalkyl acrylates from fluoroacetic esters", Tetrahedron, Elsevier Science Publishers, Amsterdam, NL, vol. 63, No. 9, Jan. 25, 2007 (Jan. 25, 2007), pp. 2042-2046.*

Aimee R. Usera et al, Unexpected Steric Effects of 'Remote' Alkyl Groups on the Rate of Conjugate Additions to Alkyl [alpha], [beta]-Ethylenic Sulfones, Sulfoxides and Esters, The Journal of Organic Chemistry, Mar. 1, 2007, pp. 2329-2334, vol. 72, No. 7, EP.

Bevilacqua, Pat F. et al, Sulfazecin Analogues. Preparation of 4-(Trifluoromethyl)-1-sulfo-2-azetidinone Derivates, J. Org. Chem., 1984, pp. 1430-1434, 49.

Christoph Börner er al, Copper-Catalyzed Asymmetric 1,4-Addition of Organozinc Compounds to Linear aliphatic Enones, European Journal of Organic Chemistry, Jun. 5, 2001, pp. 2435-2446, vol. 2001, No. 13, EP.

Extended European search report for application 14169288 dated Nov. 20, 214, 4 pages.

International Search report for PCT/EP2015/061038, dated Jul. 17, 2015, 16 pages.

Taber F et al, Enantioselective Construction of Cyclic Quaternary Centers: -Mesembrine, The Journal of Organic Chemistry, Jan. 1, 2001, pp. 143-147, vol. 66, EP.

Tamura K et al, The effect of fluoromethyl groups on the diastereoselectivity in the electrophillic alkylation, Journal of Fluorine Chemistry, Jun. 1, 2005, pp. 918-930, vol. 126 No. 6, EP.

Yadav JS et al, A Facile Conversion of Tertiary Alcohols to Olefins, Synthetic Communications, Jan. 1, 1989, pp. 1057-1060, vol. 19, No. 5-6, EP.

Yamazaki T et al, Stereoselective preparation of ethyl, Tetrahedron Asymmetry, Jan. 1, 1990, pp. 521-524, vol. 1, No. 8, EP.

* cited by examiner

*Primary Examiner* — Deborah D Carr

(57) ABSTRACT

A process to prepare a compound of Formula (I)

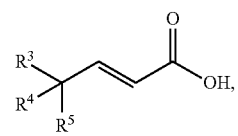

Formula (I)

wherein $R^3$, $R^4$ and $R^5$ are each selected independently from hydrogen, halogen, alkyl, alkenyl, alkynyl, alkoxyl, and wherein the alkyl, alkenyl, alkynyl, and alkoxyl may be optionally substituted with one or more halogen, alkyl, alkenyl, alkynyl, and alkoxyl.

18 Claims, No Drawings

PROCESS FOR PREPARING SUBSTITUTED CROTONIC ACIDS

CROSS-REFERENCE TO RELATED APPLICATIONS

This application is a continuation application of U.S. application Ser. No. 15/312,013, filed Nov. 17, 2016 which was a national stage entry under 35 U.S.C. § 371 of PCT/EP2015/061038, filed on May 20, 2015, which claims priority to EP Application No. EP14169288.9, filed on May 21, 2014, the content of PCT/EP2015/061038 is hereby incorporated by reference in its entirety.

BACKGROUND

WO2012/041872 discloses novel N-heteroaryl compounds that are useful as medicaments. This patent application also discloses the dehydration of ethyl 4,4,5,5-tetrafluoro-3-hydroxy-pentanoate to ethyl (E)-4,4,5,5-tetrafluoropent-2-enoate using phosphorous pentoxide ($P_2O_5$).

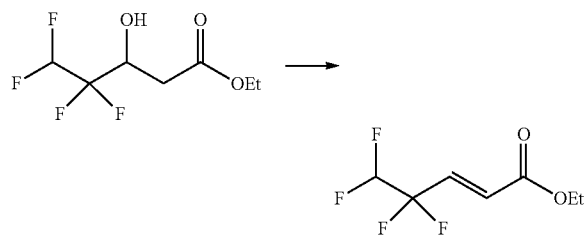

WO2012/041873 discloses novel N-heteroaryl compounds that are useful as medicaments. This patent application also discloses the dehydration of ethyl 4,4,5,5-pentafluoro-3-hydroxy-pentanoate to ethyl (E)-4,4,5,5-pentafluoropent-2-enoate using phosphorous pentoxide ($P_2O_5$).

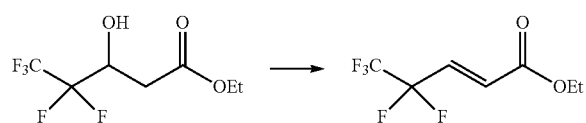 [SMILES: CCOC(=O)CC(O)C(F)(F)C(F)(F)F ; CCOC(=O)/C=C/C(F)(F)C(F)(F)F]

WO2013/144179 discloses novel heteroaryl compounds that are useful as medicaments. This patent application also discloses the dehydration of ethyl 4,4 difluoro-3-hydroxy-pentanoate to ethyl (E)-4,4-difluoropent-2-enoate using diphenyl-2-pyridylphosphine and di-butylazodicarboxylate.

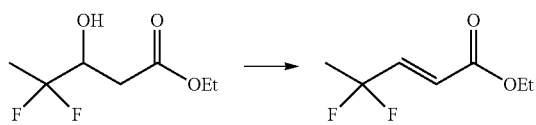

WO2013/144180 discloses novel heteroaryl compounds that are useful as medicaments. This patent application also discloses the dehydration of ethyl 4,4 difluoro-3-hydroxy-pentanoate to ethyl (E)-4,4-difluoropent-2-enoate using diphenyl-2-pyridylphosphine and di-butylazodicarboxylate.

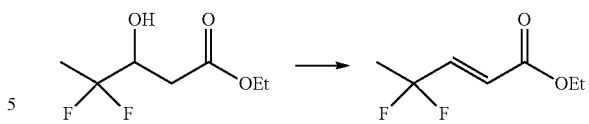

Jagodzinska et al. Tetrahedron 63 (2007) 2042-2046 discloses the synthesis of crotonic acid analogues according to the following route:

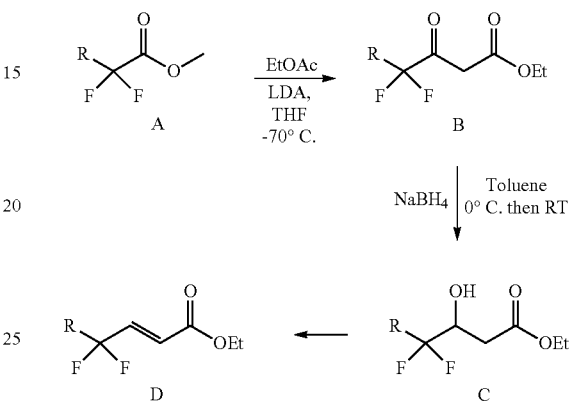

wherein the dehydration reaction from C to D, the reagent used was $P_2O_5$. Moreover, this reference discloses that this reaction was also attempted using mesyl chloride and triethylamine for the transformation of C to D. However, the desired product (D) was only obtained as a minor product in a mixture of carboxylic acids. $H_2SO_4$, $H_2SO_4$/AcOH, $SOCl_2$ and DBU/$CHCl_3$ were also unsuccessfully used as reagents for the dehydration reaction. R=F, H, $CF_3$, Cl, Br, or I.

Bevilaqua, J. Org. Chem. 49 (1984) 1430-1434 discloses a dehydration reaction using triphenylphosphine and diethyl azodicarboxylate (DEAD) as reagents.

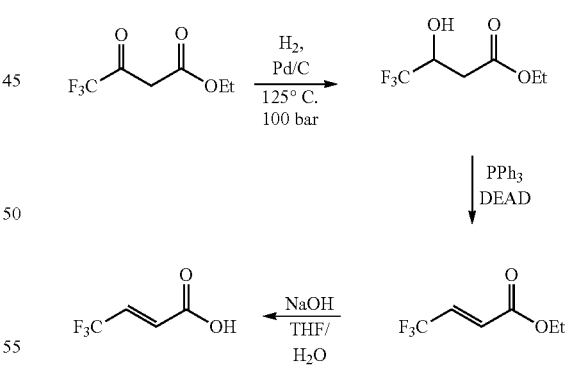

Tamura et al. Journal of Fluorine Chemistry 126 (2005) 918-930 discloses a dehydration reaction using tosyl choride and triethylamine (TEA)

Yamazaki et al., Tetrahedron: Asymmetry 1 (1990) 521-524 also discloses a dehydration reaction using tosyl choride and triethylamine (TEA).

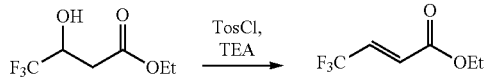 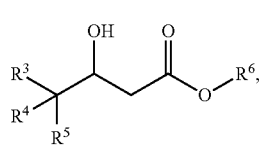

SUMMARY OF THE INVENTION

This invention relates to an improved process for making crotonic acid intermediates which can be used to make compounds that can be used as medicaments.

An embodiment of the invention is a process to prepare a compound of Formula (I)

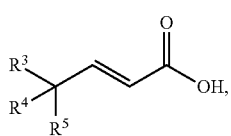

Formula (I)

wherein $R^3$, $R^4$ and $R^5$ are each selected independently from hydrogen, halogen, alkyl, alkenyl, alkynyl, alkoxyl, and wherein the alkyl, alkenyl, alkynyl, and alkoxyl may be optionally substituted with one or more halogen, alkyl, alkenyl, alkynyl, and alkoxyl;
comprising
a) reacting a compound of Formula (V)

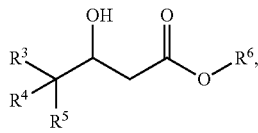

Formula (V)

wherein $R^3$, $R^4$ and $R^5$ are defined as above, and $R^6$ is alkyl;
with methane sulfonyl chloride and a base to form a compound of Formula (VI)

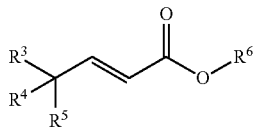

Formula (VI)

wherein $R^3$, $R^4$, $R^5$ and $R^6$ are defined as above; and
b) reacting the compound of Formula (VI) with a reagent to form a compound of Formula (I).

Another embodiment of the process is wherein the base of step a) is an amine. In yet another embodiment, the amine is triethylamine.

Another embodiment of the process is wherein the reagent of step b) is an acid or a base. In yet another embodiment of the process, the reagent is a base. In further embodiments, the base is sodium hydroxide, lithium hydroxide or potassium hydroxide. In an embodiment, the base is sodium hydroxide.

In an alternative embodiment, the process further comprises a process for preparing a compound of Formula (V)

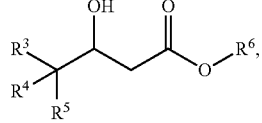

Formula (V)

wherein $R^3$, $R^4$, $R^5$, and $R^6$ are defined as above;
comprising
i. reacting a compound of Formula (II)

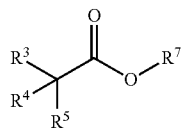

Formula (II)

wherein $R^3$, $R^4$ and $R^5$ are defined as above and $R^7$ is alkyl; with a compound of Formula (III)

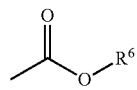

Formula (III)

wherein $R^6$ is alkyl,
and a base to form a compound of Formula (IV)

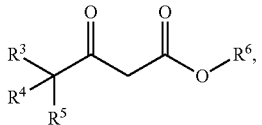

Formula (IV)

wherein $R^3$, $R^4$, $R^5$ and $R^6$ are defined as above; and
ii. reducing the compound of Formula (IV) with a reducing agent to form a compound of Formula (V).

In another embodiment, the base of step i) is LiHMDS, sodium hydride, LDA, KOtBu or NaOEt.

In yet another embodiment, the reducing agent of step ii) is lithium borohydride, sodium borohydride, disiamylborane, hydrogen with platinum (IV) oxide, hydrogen with palladium/carbon or zinc borohydride. In an embodiment, the reducing agent is sodium borohydride.

In another embodiment, at least one of $R^3$, $R^4$ and $R^5$ is halogen. In another embodiment, the halogen is bromine, chlorine or fluorine. In another embodiment, at least one of $R^3$, $R^4$ and $R^5$ is alkyl. In another embodiment, $R^3$ is $CH_3$ and $R^4$ and $R^5$ are both fluorine. In another embodiment, $R^3$ is Cl and $R^4$ and $R^5$ are both fluorine. In another embodiment, $R^3$ is Br and $R^4$ and $R^5$ are both fluorine. In another embodiment, $R^3$ is $CF_3$, $R^4$ is $CH_3O$ and $R^5$ is fluorine. In another embodiment, $R^3$ is $CH_3$ and $R^4$ and $R^5$ are both chlorine. In another embodiment, $R^3$ is $CF_3$, $R^4$ is chlorine and $R^5$ is fluorine. In another embodiment, $R^3$ and $R^4$ are both fluorine $R^5$ is hydrogen.

In another embodiment, $R^3$ is $CHF_2$, $R^4$ and $R^5$ are fluorine.

In another embodiment, $R^6$ is ethyl. In another embodiment, $R^7$ is ethyl. In another embodiment, $R^7$ is methyl.

DETAILED DESCRIPTION

Compounds of Formula (I) which are analogs of crotonic acid are useful as intermediates for the production of compounds which are useful as medicaments.

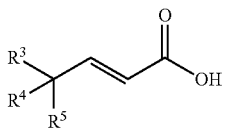

Formula (I)

The syntheses of crotonic acid analogs are known. WO2012/041872, WO2012/041873, WO2013/144179 and WO2013/144180, among others, disclose processes to prepare substituted pent-2-enoates and but-2-enoates from the corresponding 3-hydroxy-pentanoates and 3-hydroxy-butanoates, respectively.

In these applications, phosphorous pentoxide ($P_2O_5$) or diphenyl-2-pyridylphosphine and di-butylazodicarboxylate were used as reagents for these dehydration reactions. Other references have disclosed the use of triphenylphosphine and diethyl azodicarboxylate (DEAD) or tosyl chloride and triethylamnine as reagents for similar reactions (see Jagodzinska, Bevilaqua, Tamura and Yamazaki above). These reagents offer several disadvantages when the process is conducted on commercial scale.

When triphenylphosphine and diethylazodicarboxylate are used for the dehydration reaction, byproducts (triphenylphosphine oxide and diethoxycarboxyhydrazine) are formed which make purification of the desired reaction product difficult. Chromatographic separation is often required which is undesired and often impractical at a commercial scale. Moreover, diethylazodicarboxylate is an expensive reagent that is light and oxygen sensitive and thermally unstable which can lead to uncontrollable runaway reactions. Transport of this reagent is severely restricted and limited to only solutions, not the pure form. Triphenylphosphine is also sensitive against oxygen and air. Furthermore, it generates large waste streams due to an unfavourable mass balance.

Diphenyl-2-pyridylphosphine and di-butylazodicarboxylate have been used as alternatives to triphenylphosphine and diethylazodicarboxylate for the dehydration reaction (see WO2013/144179 and WO2013/144180). However, the cost of these reagents is prohibitive for a commercial process.

The phosphorpentoxide reagent ($P_2O_5$) reagent used in the dehydration reactions of the cited references (see WO2012/041872 and WO2012/041873) is a solid and was used in the cited references without any solvent. On a large scale, efficient mixing of solids is not possible. Moreover, when solids are mixed there is little dissipation of generated reaction heat, and this poses a severe safety risk.

Tosylchloride is also a solid and as noted above with $P_2O_5$ is more difficult to handle on a larger scale than the scale of the reactions disclosed in the cited references (see Tamura et al. and Yamazaki et al.). Furthermore, precautions must be taken to avoid exposure to dust. Liquids are easier to handle on large scale, especially in a production environment.

There is a need for alternative reagents to conduct the dehydration reaction of substituted 3-hydroxy-pentanoates and 3-hydroxy-butanoates to form the corresponding pent-2-enoates and but-2-enoates, especially on a commercial scale. Applicants have found that methane sulfonyl chloride is unexpectedly a suitable reagent for this transformation.

An embodiment of the invention is a process to prepare a compound of Formula (I)

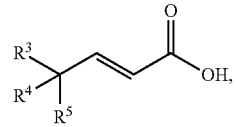

Formula (I)

wherein $R^3$, $R^4$ and $R^5$ are each selected independently from hydrogen, halogen, alkyl, alkenyl, alkynyl, alkoxyl, and wherein the alkyl, alkenyl, alkynyl, and alkoxyl may be optionally substituted with one or more halogen, alkyl, alkenyl, alkynyl, and alkoxyl;

comprising
a) reacting a compound of Formula (V)

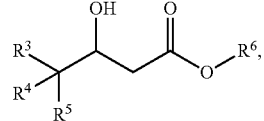

Formula (V)

wherein $R^3$, $R^4$ and $R^5$ are defined as above, and $R^6$ is alkyl;
with methane sulfonyl chloride and a base to form a compound of Formula (VI)

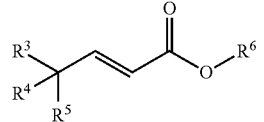

Formula (VI)

wherein $R^3$, $R^4$, $R^5$ and $R^6$ are defined as above; and
b) reacting the compound of Formula (VI) with a reagent to form a compound of Formula (I).

Another embodiment of the process is wherein the base of step a) is an amine. In yet another embodiment, the amine is triethylamine.

Another embodiment of the process is wherein the reagent of step b) is an acid or a base. In yet another embodiment of the process, the reagent is a base. In further embodiments, the base is sodium hydroxide, lithium hydroxide or potassium hydroxide. In an embodiment, the base is sodium hydroxide.

Suitable solvents for step b) comprise solvents that are miscible with water like THF, EtOH, MeOH or isopropanol. In one embodiment, the reaction of step b) is done in a mixture of such a solvent and water. Other suitable solvents comprise solvents that are immiscible with water like toluene. In another embodiment, the reaction of step b) is done in a mixture of such a solvent with water such that a biphasic mixture is used.

Suitable reaction temperatures for step b) range from −10° C. to 60° C. In an embodiment, the temperature range is from 0° C. to 25° C. In another embodiment, the temperature range is from 25° C. to 40° C. In another embodiment, the temperature range is from 40° C. to 50° C.

In step a) methanesulfonic acid chloride is used advantageously in excess related to (V) in a ratio of 1:1 to 2:1. In other embodiments, the methane sulfonic acid chloride is used in a ratio of 1:1 to 1.5:1 or in a ratio of 1.25:1 to 1.3:1 or in a ratio of 1.05 to 1.1.

The base in step a) is used advantageously in excess related to (V) in a ratio of 2:1 to 8:1, In other embodiments, the ratio is 2:1 to 5:1, or the ratio is 2:1 to 3:1. The reaction of step a) can be performed in such a way that the base is added in one portion or can be performed in a stepwise manner: advantageously compound (V) is combined with 1 to 1.2 equivalents of base followed by the addition of MesCl followed by additional base.

Suitable temperature for the addition of MesCl in step a) ranges from −10° C. to 25° C. In another embodiment, the temperature is from −5° C. to 0° C. In another embodiment the temperature is from 0° C. to 10° C. Following the addition of MesCl, the reaction is stirred at a suitable temperature to complete formation of the intermediate methane sulfonic ester of (V). Suitable temperature for this reaction ranges from 0° C. to 30° C. Afterwards, the remaining excess of base is added. Suitable temperature for the addition of the excess base ranges from −10° C. to 25° C. In another embodiment, the suitable temperature for the addition of the excess base ranges from 0° C. to 25° C. After complete addition of base, the reaction mixture is stirred to allow complete formation of compound (VI). Suitable temperature for this stirring period ranges from 0° C. to 40° C. In another embodiment, the suitable temperature for the stirring period ranges from 10° C. to 25° C. In another embodiment, the suitable temperature for the stirring period ranges from 20° C. to 30° C.

Suitable solvents for step a) include halogenated solvents like dichloromethane (DCM), chloroform, dichloroethane and other solvents like tetrahydrofuran (THF), 2-methyl-THF, toluene, benzene, EtOAc. In an embodiment, the solvent is DCM. In another embodiment, the solvent is toluene.

In one embodiment the solvents for steps a) and b) are different. In another embodiment, the solvent for step a) is the same as for step b).

In an embodiment, the base used is triethyl amine, the solvent used is DCM and the temperature of the reaction is from 0° C. to 25° C. In another embodiment, the base used is triethyl amine, the solvent used is DCM and the temperature of the reaction is from 0° C. to 25° C. and the triethyl amine is added stepwise, a portion being added before or with the methane sulfonyl chloride and a portion being added after the addition of the methane sulfonyl chloride. In another embodiment, the base used is triethylamine, the solvent used is toluene and the temperature of the reaction is from 0° C. to 30° C. In yet another embodiment, the base used is triethylamine, the solvent used is toluene and the temperature of the reaction is from 0° C. to 30° C. and the triethyl amine is added stepwise, a portion being added before or with the methane sulfonyl chloride and a portion being added after the addition of the methane sulfonyl chloride.

The raw product (VI) can be purified or used without purification in the next step. Methods for purification include chromatography on silica or distillation. In an embodiment, the raw product (VI) is purified by distillation. In another embodiment, the distillation is at reduced pressure. In another embodiment, the distillation is performed in a short path distillation equipment. In yet another embodiment, the raw product (VI) is used directly in step b)

In an embodiment, the yield for step a) ranges from 40% to 90%. In another embodiment, the yield ranges from 50% to 85%. In another embodiment, the yield ranges from 60% to 80%.

In an alternative embodiment, the process further comprises a process for preparing a compound of Formula (V)

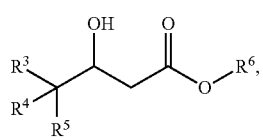

Formula (V)

wherein $R^3$, $R^4$, $R^5$, and $R^6$ are defined as above;
comprising
i) reacting a compound of Formula (II)

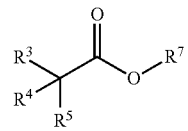

Formula (II)

wherein $R^3$, $R^4$ and $R^5$ are defined as above and $R^7$ is alkyl; with a compound of Formula (III)

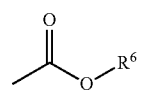

Formula (III)

wherein $R^6$ is alkyl,
and a base to form a compound of Formula (IV)

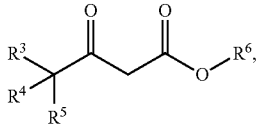

Formula (IV)

wherein $R^3$, $R^4$, $R^5$ and $R^6$ are defined as above; and
ii) reducing the compound of Formula (IV) with a reducing agent to form a compound of Formula (V).

In another embodiment, the base of step i) is LiHMDS, sodium hydride, LDA, KOtBu or NaOEt.

Step i) is preferably done in a solvent. The solvent can be an ether-derived solvent like diethyl ether, methyl tert-butyl ether, THF, 2-methyl-THF, 1,4-dioxane or cyclopentyl methyl ether or a hydrocarbon solvent like toluene. The reaction temperature can range from −78° C. to 80° C., preferably from 0° C. to 65° C. In an embodiment the temperature ranges from 50° C. to 60° C. The raw product of compound (IV) is typically subjected to an aqueous quench or work-up which can include the addition of a solution of an acid like hydrochloride acid or ammonium chloride or the addition of a base like sodium carbonate or sodium bicarbonate or the simultaneous addition of an acid and a base. Following the quench or work-up, the raw product (IV) can be used directly in step ii). In another embodiment, compound (IV) is isolated and then used in step ii). In yet another embodiment, compound (IV) is isolated and purified by distillation or column chromatography and then used in step ii).

In yet another embodiment, the reducing agent of step ii) is lithium borohydride, sodium borohydride, disiamylborane, hydrogen with platinum (IV) oxide, hydrogen with palladium/carbon or zinc borohydride. In an embodiment, the reducing agent is sodium borohydride.

Suitable solvents for step ii) include ether-derived solvent like diethyl ether, methyl tert-butyl ether, THF, 2-methyl-THF, 1,4-dioxane or cyclopentyl methyl ether or inert solvents like toluene. In one embodiment the solvents for steps i) and ii) are different. In another embodiment, the solvent for step i) is the same as for step ii).

The reducing agent for step ii) is added at a temperature that can range from −10° C. to 25° C. In an embodiment, the addition is done at 0° C., in another embodiment the addition is done at a temperature from 20° C. to 25° C. After the addition of the reducing agent, the reaction in step ii) is continued at a temperature that ranges from −10° C. to 25° C. In one embodiment, the reaction is continued at 0° C., in another embodiment the reaction is continued at a temperature from 20° C. to 25° C.

In another embodiment, steps i), ii), a) and b) of the process are conducted without isolation of the intermediate compounds of Formulas (IV), (V) or (VI).

In another embodiment, at least one of $R^3$, $R^4$ and $R^5$ is halogen. In yet other embodiments, the halogen is bromine, chlorine or fluorine.

In further embodiments, at least one of $R^3$, $R^4$ and $R^5$ is alkyl. In another embodiment, $R^3$ is $CH_3$ and $R^4$ and $R^5$ are both fluorine. In yet another embodiment, $R^3$ is Cl and $R^4$ and $R^5$ are both fluorine. In another embodiment, $R^3$ is Br and $R^4$ and $R^5$ are both fluorine. In an embodiment, $R^3$ is $CF_3$, $R^4$ is $CH_3O$ and $R^5$ is fluorine. In yet another embodiment, $R^3$ is $CH_3$ and $R^4$ and $R^5$ are both chlorine. In another embodiment, $R^3$ is $CF_3$, $R^4$ is chlorine and $R^5$ is fluorine.

In an embodiment, $R^6$ is ethyl. In another embodiment, $R^7$ is ethyl. In yet another embodiment, $R^7$ is methyl.

The following definitions are provided to more clearly describe the invention.

"Alkyl" means an aliphatic hydrocarbon group which may be straight or branched and comprising about 1 to about 20 carbon atoms in the chain. In one embodiment alkyl groups contain about 1 to about 12 carbon atoms in the chain. In another embodiment alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. Non-limiting examples of suitable alkyl groups include methyl, ethyl, n-propyl, isopropyl, n-butyl, t-butyl, n-pentyl, heptyl, nonyl, or decyl.

"Alkylene" means a divalent group obtained by removal of a hydrogen atom from an alkyl group that is defined above. Non-limiting examples of alkylene include methylene, ethylene and propylene. In one embodiment, alkylene groups have about 1-18 carbon atoms in the chain, which may be straight or branched. In another embodiment, alkylene groups have about 1-12 carbon atoms in the chain, which may be straight or branched. In another embodiment, alkylene groups may be lower alkylenes. "Lower alkylene" means an alkylene having about 1 to 6 carbon atoms in the chain, which may be straight or branched.

"Alkenyl" means an aliphatic hydrocarbon group containing at least one carbon-carbon double bond and which may be straight or branched and comprising about 2 to about 15 carbon atoms in the chain. In one embodiment alkenyl groups have about 2 to about 12 carbon atoms in the chain. In another embodiment alkenyl groups have about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. The term "substituted alkenyl" means that the alkenyl group may be substituted by one or more substituents which may be the same or different, each substituent being independently selected from the group consisting of halo, alkyl, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkynyl" means an aliphatic hydrocarbon group containing at least one carbon-carbon triple bond and which may be straight or branched and comprising about 2 to about 15 carbon atoms in the chain. In one embodiment alkynyl groups have about 2 to about 12 carbon atoms in the chain. In another embodiment alkynyl groups have about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl, 3-methylbutynyl, n-pentynyl, and decynyl. The term "substituted alkynyl" means that the alkynyl group may be substituted by one or more substituents which may be the same or different, each substituent being independently selected from the group consisting of alkyl, aryl and cycloalkyl.

"Halo" (or "halogeno" or "halogen") means fluoro, chloro, bromo, or iodo groups. Preferred are fluoro, chloro or bromo, and more preferred are fluoro and chloro.

"Haloalkyl" means an alkyl as defined above wherein one or more hydrogen atoms on the alkyl are replaced by a halo group as defined above.

"Alkoxy" means an —O-alkyl group in which the alkyl group is as previously described. Non-limiting examples of suitable alkoxy groups include methoxy, ethoxy, n-propoxy, isopropoxy, n-butoxy and heptoxy. The bond to the parent moiety is through the ether oxygen.

With reference to the number of moieties (e.g., substituents, groups or rings) in a compound, unless otherwise defined, the phrases "one or more" and "at least one" mean that there can be as many moieties as chemically permitted, and the determination of the maximum number of such moieties is well within the knowledge of those skilled in the art.

When used herein, the term "independently", in reference to the substitution of a parent moiety with one or more substituents, means that the parent moiety may be substituted with any of the listed substituents, either individually or in combination, and any number of chemically possible substituents may be used.

The term "substituted" means that one or more hydrogens on the designated atom is replaced with a selection from the indicated group, provided that the designated atom's normal valency under the existing circumstances is not exceeded, and that the substitution results in a stable compound.

Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

"Solvate" means a physical association of a compound of this invention with one or more solvent molecules. Non-limiting examples of suitable solvates include ethanolates, methanolates, and the like. "Hydrate" is a solvate wherein the solvent molecule is $H_2O$.

The term "salt(s)", as employed herein, denotes acidic salts formed with inorganic and/or organic acids, as well as basic salts formed with inorganic and/or organic bases.
TEA is triethylamine.
DCM is dichloromethane.
THF is tetrahydrofuran.
EtOH is ethanol.
MeOH is methanol.
EtOAc is ethyl acetate.
Mesyl chloride or MesCl or MSC means methane sulfonyl chloride or methanesulfonic acid chloride.
Tosyl chloride means p-toluene sulfonyl chloride.
Reducing agent—Non-limiting examples of reducing agents are lithium borohydride, sodium borohydride, disiamylborane, hydrogen with platinum(IV) oxide, hydrogen with palladium/carbon, zinc borohydride and the like.

EXAMPLES

Example 1

Synthesis of (E)-4-bromo-4,4-difluoro-but-2-enoic acid

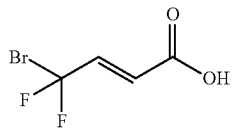

Step A: Ethyl 4-bromo-4,4-difluoro-3-oxo-butanoate

Lithium bis(trimethylsilyl)amide (200 ml of a 1M solution in THF, 0.2 mol) was cooled to −75° C. with stirring. A mixture of ethyl acetate (17 ml, 0.19 mol) and THF (15 ml) was charged with stirring over one hour while keeping the temperature at −75° C. A mixture of ethyl 2-bromo-2,2-difluoroacetate (20 g, 0.099 mol) and THF (20 ml) was charged over one hour at the same temperature. The reaction mixture was quenched with a saturated aqueous solution of $NH_4Cl$ (150 ml) forming a slurry, the cooling bath was removed and the reaction mixture was allowed to reach room temperature overnight while stirring was continued. The mixture was acidified with aqueous HCl (1M) and the layers separated. The aqueous layer was extracted with EtOAc, the organic phases were combined, washed two times with aqueous HCl (1M) and with brine, dried over $MgSO_4$ and concentrated under reduced pressure. The residue was distilled under reduced pressure (6 mbar, 75° C.) to yield 19.1 gram (79% yield). $^1$H-NMR (600 MHz, $CDCl_3$): δ 11.94 (s), 5.46 (s), 4.19 (q, J=7.1 Hz), 4.16 (q, J=7.2 Hz), 3.71 (s), 1.24 (t, J=7.1 Hz), 1.21 (t, J=7.1 Hz), $^{19}$F-NMR (564 MHz, $CDCl_3$): δ −59.1 (s), −65.0 (s)

Step B: Ethyl 4-bromo-4,4-difluoro-3-hydroxy-butanoate

Ethyl 4-bromo-4,4-difluoro-3-oxo-butanoate (18 g from step A, 0.073 mol) was dissolved in toluene (200 ml) and cooled in an ice bath. Sodium borohydride (3.03 g, 0.08 mol) was charged portionwise with stirring. After 15 minutes, the ice bath was removed and the mixture was allowed to reach room temperature overnight while stirring was continued. The mixture was filtered, the filter residue washed with toluene, the filtrates were combined, cooled in an ice bath and acidified with HCl (1M). The layers were separated and the aqueous layer was extracted with EtOAc (2 times). The combined organic layers were washed with brine, dried over $MgSO_4$ and concentrated under reduced pressure. The residue was dissolved in methanol and the mixture evaporated to dryness to yield 16.35 gram (90% yield). $^1$H-NMR (600 MHz, $CDCl_3$): δ 4.27-4.37 (m, 1 H), 4.13 (q, J=7.1 Hz, 1H), 2.71 (dd, J=16 Hz, 3.1 Hz, 1H), 2.59 (dd, J=16 Hz, 9 Hz, 1H), 1.21 (t, J=7.1 Hz, 3H); $^{19}$F-NMR (564 MHz, $CDCl_3$): δ −57.4 (dd, J=165 Hz, 8 Hz), −60.0 (dd, J=164 Hz, 8 Hz); MS 201, 203 $[M-OC_2H_5]^+$.

Step C: Ethyl (E)-4-bromo-4,4-difluoro-but-2-enoate

Ethyl 4-bromo-4,4-difluoro-3-hydroxy-butanoate (15.3 g from step B, 0.062 mol) was combined with DCM (200 ml) and TEA (8.6 ml, 0.062 mol) and cooled in an ice bath. A solution of methanesulfonic acid chloride (7.24 ml, 0.093 mol) in DCM (50 ml) was charged with stirring while the temperature was kept between 5° C. and 10° C. After the addition was complete, the cooling bath was removed and the mixture was stirred at ambient temperature for 4 hours. The mixture was cooled in an ice bath and TEA (17.3 ml, 0.124 mol) was charged dropwise. After the addition was complete, the cooling bath was removed and the mixture was stirred overnight at ambient temperature. Water (50 ml) was added to the mixture with stirring, the layers were separated. The organic layer was washed with HCl (1N, 50 ml, 2 times), brine, dried over $MgSO_4$ and concentrated under reduced pressure. The residue was distilled under reduced pressure (4.5 mbar, 70° C.) to yield 10.9 g (77% yield). $^1$H-NMR (600 MHz, $CD_3CN$): δ 6.97 (dt, J=16 Hz, 10 Hz, 1H), 6.27 (dt, J=16 Hz, 2 Hz, 1H), 4.13 (q, J=7.1 Hz, 2H), 1.18 (t, J=7.1 Hz, 3H), $^{19}$F-NMR (564 MHz, $CD_3CN$): δ −50.3 (d, J=11 Hz), MS 183, 185 $[M-OC_2H_5]^+$.

Step D: (E)-4-bromo-4,4-difluoro-but-2-enoic acid

NaOH (4M, 19 ml, 0.076 mol) was added to a mixture of ethyl (E)-4-bromo-4,4-difluoro-but-2-enoate (9.9 g of step C, 0.043 mol) in EtOH (50 ml) and stirred at ambient temperature for two hours. The mixture was acidified with HCl (6M, 18 ml). EtOAc (80 ml) was added and after 5 minutes of stirring phase separation was observed. The layers were separated, the organic layer was washed with brine, dried over $MgSO_4$ and concentrated under reduced pressure to yield 7.84 g of a solid (90% yield). $^1$H-NMR (300 MHz, $CD_3CN$): δ 7.07 (dt, J=16 Hz, 10 Hz, 1H), 6.36 (dt, J=16 Hz, 2 Hz, 1H), $^{19}$F-NMR (282 MHz, $CD_3CN$): δ −50.3 (d, J=10 Hz), MS 199, 201 (M-1).

Example 2

Synthesis of (E)-4,4-difluorobut-2-enoic acid

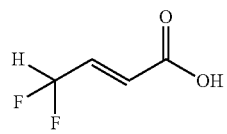

Step A: Ethyl 4,4-difluoro-3-oxo-butanoate

Sodium hydride (60% dispersion in mineral oil, 10.7 g, 0.267 mol) was suspended in THF (anhydrous, 300 ml) under a nitrogen atmosphere. The mixture was cooled to 0° C. with stirring, ethyl acetate (26 ml, 0.267 mol) was charged over 20 min. and stirring was continued for one hour. Ethyl 2,2-difluorobutanoate (16.1 g, 0.13 mol) was dissolved in THF (anhydrous, 20 ml) and this solution was charged with stirring over 20 min while the temperature was kept at 0° C. Stirring was continued for three hours at 0° C., the cooling bath was removed and the mixture stirred at room temperature for two days. The mixture was cooled to 0° C. and quenched with a saturated aqueous solution of $NH_4Cl$ (60 ml) forming a slurry. Hydrochloric acid was added (2M, 60 ml), the layers were separated, and the aqueous layer was extracted with diethylether (50 ml, three times). The combined organic layers were washed two times with hydrochloric acid (2M), brine, dried over $Na_2SO_4$ and concentrated under reduced pressure. The residue was distilled under reduced pressure (25 mbar, 52-62° C.) to yield 16.4 gram of a liquid (0.099 mol, 76% yield). $^1$H-NMR (300 MHz, $CDCl_3$): δ 11.8 (s), 5.72-6.22 (m), 5.50 (s), 4.21-4.31 (m), 3.71 (m), 1.27-1.35 (m); $^{19}$F-NMR (282 MHz, $CDCl_3$): δ −126.4 (d, J=54 Hz), −127.8 (d, J=53 Hz); MS 121 (M-$OCH_2CH_3$)

Step B: Ethyl 4,4-difluoro-3-hydroxy-butanoate

Ethyl 4,4-difluoro-3-oxo-butanoate (16 g from step A, 0.096 mol) was dissolved in toluene (250 ml) and cooled in an ice bath. Sodium borohydride (4 g, 0.106 mol) was charged portionwise with stirring. After 15 minutes, the ice bath was removed and the mixture was allowed to reach room temperature overnight while stirring was continued. The mixture was filtered, the filter residue washed with toluene, the filtrates were combined, cooled in an ice bath and acidified with HCl (1M). The layers were separated and the aqueous layer was extracted with EtOAc (2 times). The combined organic layers were washed with brine, dried over $MgSO_4$ and concentrated under reduced pressure. The residue was dissolved in methanol and the mixture evaporated to dryness to yield 9 gram of a liquid (0.053 mol, 56% yield). $^1$H-NMR (300 MHz, $CDCl_3$): δ 5.78 (td, J=56 Hz, 3.7 Hz, 1H), 4.32 (m, 1H), 4.13 (q, J=7.1 Hz, 2H), 2.71 (m, 1H), 2.59 (m, 1H), 1.21 (t, J=7.1 Hz, 3H); $^{19}$F-NMR (282 MHz, $CDCl_3$): δ −128.7 (ddd, J=288 Hz, 56 Hz, 10 Hz), −131.7 (ddd, J=288 Hz, 56 Hz, 12 Hz); MS 123 (M-$OCH_2CH_3$)

Step C: Ethyl (E)-4,4-difluoro-but-2-enoate

Ethyl 4,4-difluoro-3-hydroxy-butanoate (9 g from step B, 0.053 mol) was dissolved in DCM (100 ml) followed by the addition of TEA (7.46 ml, 0.053 mol) and cooled in an ice bath. A solution of methanesulfonic acid chloride (6.26 ml, 0.08 mol) in DCM (25 ml) was added dropwise with stirring while the temperature was kept between 0° C. and 5° C. After the addition was complete, the cooling bath was removed and the mixture was stirred at ambient temperature for 4 hours. The mixture was cooled in an ice bath and TEA (14.9 ml, 0.107 mol) was added dropwise. After the addition was complete, the cooling was removed and the mixture was stirred overnight at ambient temperature. Water (50 ml) was added to the mixture with stirring, the layers were separated. The organic layer was washed with HCl (1N, 50 ml, 3 times), brine, dried over $MgSO_4$ and concentrated under reduced pressure. The residue was distilled under reduced pressure (37 mbar, 58-60° C.) to yield 3.6 g (0.022 mol, 40% yield). $^1$H-NMR (300 MHz, $CDCl_3$): δ 6.75-6.85 (m, 1H), 6.29 (dt, J=16 Hz, 2.9 Hz, 1H), 6.14 (td, J=55 Hz, 4.2 Hz, 1H), 4.26 (q, J 7.1 Hz, 2H), 1.32 (t, J=7.1 Hz, 3H), $^{19}$F-NMR (282 MHz, $CD_3Cl$): δ −115.9 (ddd, J=54 Hz, 10 Hz, 3.0 Hz), MS 183, 185 [M-$OC_2H_5$]$^+$.

Step D: (E)-4,4-difluoro-but-2-enoic acid

Ethyl (E)-4,4-difluoro-but-2-enoate (3.6 g from step C, 0.024 mol) was dissolved in THF (24 ml) and cooled down to 0° C. in an ice-bath. NaOH (4N, 14 ml) was charged in one portion. The mixture was stirred for 3 h at room temperature. The layers were separated and the organic layer was extracted with NaOH (2M). The combined aqueous layers were cooled again in an ice-bath, acidified to pH 1 with hydrochloric acid (6N) and then extracted with ethyl acetate (2 times). The combined organic layers were washed with brine, dried over $Na_2SO_4$ and concentrated under reduced pressure. The residue was dissolved in methyl tert-butyl ether, washed with HCl (1N, 2 times) and then extracted with NaOH (2N, 4 times). The combined aqueous extracts were washed with methyl tert-butyl ether (3 times), acidified with HCl (10%) and extracted with methyl tert-butyl ether (4 times). The combined organic extracts were dried over $Na_2SO_4$ and evaporated under reduced pressure to yield 2.22 g (0.0182 mol, 76%). $^1$H-NMR (300 MHz, $CDCl_3$): δ 11.70 (s), 6.83 (ddt, J=16 Hz, 10 Hz, 4 Hz, 1H), 6.22 (ddt, J=16 Hz, 3 Hz, 1 Hz, 1H), 6.18 (ddt, J=55 Hz, 4 Hz, 1 Hz, 1H); $^{19}$F-NMR (282 MHz, $CD_3Cl$): δ −116.8 (ddd, 54 Hz, 10 Hz, 3 Hz); MS 121 (M-H).

Example 3

Synthesis of (E)-4,4,5,5,5-pentafluoropent-2-enoic acid

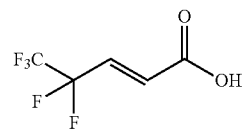

Step A: Ethyl 4,4,5,5,5-pentafluoro-3-oxo-pentanoate

Sodium ethoxide (7.49 g, 0.11 mol) was suspended in methyl tert-butyl ether (anhydrous, 200 ml) under nitrogen. Ethyl 2,2,3,3,3-pentafluoropropanoate (14.8 ml, 0.1 mol) was added dropwise followed by ethyl acetate (10.7 ml, 0.11 mol). Stirring was continued for 45 minutes at ambient temperature, for one hour at 50° C. and overnight at ambient temperature. The mixture was cooled to 0° C. and acidified with HCl (1M, 80 ml), brine was added (80 ml), the layers were separated, and the aqueous layer was back-extracted with in methyl tert-butyl ether (80 ml). The combined organic layers were dried over $Na_2SO_4$ and concentrated under reduced pressure to yield 14.6 gram (0.062 mol, 62% yield). $^1$H-NMR (300 MHz, $CDCl_3$): δ 11.96 (s), 5.59 (s), 4.11-4.26 (m), 3.70 (m), 1.21-1.29 (m); $^{19}$F-NMR (282 MHz, $CDCl_3$): δ −81.8 (s), −83.3 (s), −122.7 (s), −123.6 (s); MS 189 (M-$OCH_2CH_3$)

Step B: Ethyl 4,4,5,5,5-pentafluoro-3-hydroxy-pentanoate

Ethyl 4,4,5,5,5-pentafluoro-3-oxo-pentanoate (14.6 g from step A, 0.062 mol) was dissolved in toluene (250 ml) and cooled in an ice bath. Sodium borohydride (2.6 g, 0.069 mol) was added portionwise with stirring. After 15 minutes, the ice bath was removed and the mixture was allowed to reach room temperature overnight while stirring was continued. The mixture was filtered, the filter residue washed with toluene, the filtrates were combined, cooled in an ice bath and acidified with HCl (1M). The layers were separated and the aqueous layer was extracted with EtOAc (2 times). The combined organic layers were washed with brine, dried over $MgSO_4$ and concentrated under reduced pressure. The residue was dissolved in methanol and the mixture evaporated to dryness to yield 11.3 gram of a liquid (0.048 mol, 77% yield). $^1$H-NMR (300 MHz, $CDCl_3$): δ 4.43-4.55 (m, 1 H), 4.14 (q, J=7.1 Hz, 2 H), 3.86 (s, 1H), 2.59-2.71 (m, 2H), 1.22 (t, J=7.1 Hz, 3H); $^{19}$F-NMR (282 MHz, $CDCl_3$): δ −81.9 (s), −122.7 (dd, J=276 Hz, 5.8 Hz), −131.4 (dd, J=276 Hz, 18 Hz); MS 191 (M-$OCH_2CH_3$)

Step C: Ethyl (E)-4,4,5,5,5-pentafluoro-pent-2-enoate

Ethyl 4,4,5,5,5-pentafluoro-3-hydroxy-pentanoate (11.3 g from step B, 0.048 mol) was combined with DCM (120 ml) and TEA (6.67 ml, 0.048 mol) and cooled in an ice bath. A solution of methanesulfonic acid chloride (5.59 ml, 0.072 mol) in DCM (30 ml) was added dropwise with stirring while the temperature was kept between 0° C. and 5° C. After the addition was complete, the cooling bath was removed and the mixture was stirred at ambient temperature for 4 hours. The mixture was cooled in an ice bath and TEA (13.34 ml, 0.096 mol) was added dropwise. After the addition was complete, the cooling was removed and the mixture was stirred overnight at ambient temperature. Water (60 ml) was added to the mixture with stirring, the layers were separated. The organic layer was washed with HCl (1N, 50 ml, 3 times) and brine, dried over $MgSO_4$ and concentrated under reduced pressure. The residue was distilled under reduced pressure (50 mbar, 55° C.) to yield 6.5 g of an oil (0.03 mol, 62% yield). $^1$H-NMR (300 MHz, $CDCl_3$): δ 6.73 (dt, J=16 Hz, 12 Hz, 1H), 6.47 (dt, J=16 Hz, 2.0 Hz, 1H), 4.21 (q, J 7.1 Hz, 2H), 1.26 (t, J=7.1 Hz, 3H), $^{19}$F-NMR (282 MHz, $CD_3Cl$): δ −84.8 (s), −117.2 (m); MS 173 (M-$OC_2H_5$).

Step D: (E)-4,4,5,5,5-pentafluoropent-2-enoic acid (E)-Ethyl 4,4,5,5,5-pentafluoropent-2-enoate (6.5 g from step C, 0.03 mol) was dissolved in THF (30.0 ml) and cooled down to 0° C. in an ice-bath. NaOH (4N, 18 ml, 0.072 mol) was charged in one portion. The mixture was stirred for 3 h at room temperature. Then the layers were separated and the organic layer was extracted with NaOH (2M, 50 ml). The combined aqueous layers were cooled again in an ice-bath, acidified to pH 1 with hydrochloric acid (6N) and then extracted with ethyl acetate (50 ml, 2 times). The combined organic layers were washed with brine (50 ml), dried over $Na_2SO_4$ and concentrated under reduced pressure to yield 4 g of a solid (0.02 mol, 70%). $^1$H-NMR (300 MHz, $CDCl_3$): δ 6.84 (dt, J=16 Hz, 12 Hz, 1H), 6.50 (dt, J=16 Hz, 2 Hz, 1H); $^{19}$F-NMR (282 MHz, $CD_3Cl$): δ −84.6 (s), −117.5 (d, 11 Hz), MS 189 (M-H).

Example 4

Additional compounds that were synthesized using the procedure of Step C in Examples 1-3 above are presented in Table 1 below. Differences in the purification of the compounds of Formula (VI) are described in the column "Purification". The starting materials for the below compounds were prepared generally as described in Steps A and B in Examples 1-3 above.

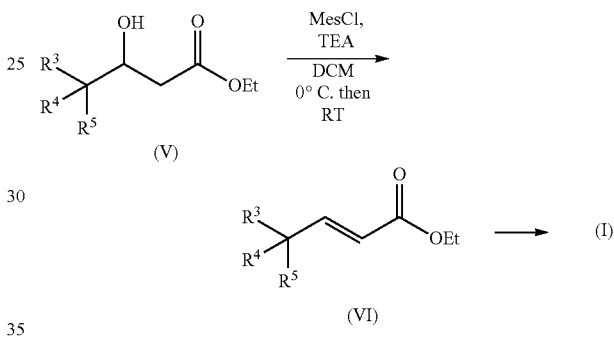

TABLE 1

| $R^3$ | $R^4$ | $R^5$ | Purification of (V) to (VI) | Yield % for step (V) to (VI) | $^1$H NMR of (I) | MS |
|---|---|---|---|---|---|---|
| Cl | F | F | as in examples above | 76 | (400 MHz; CDCl3) δ 7.05 (dt, J = 16 Hz, 9 Hz, 1H), 6.42 (dt, J = 16 Hz, 2 Hz, 1H) | 155 (M − H) |
| Me | F | F | as in examples above | 75 | (300 MHz; DMSO-$d_6$) δ 6.83 (dt, J = 16 Hz, 11 Hz 1H), 6.23 (dt, J = 16 Hz, 3 Hz, 1H), 1.79 (t, J = 19 Hz, 3H) | 137 (M + H) |
| $CF_3$ | OMe | F | Chromatography on silica column | 45 | (400 MHz; DMSO-$d_6$) δ 6.71 (dd, J = 18 Hz, 16 Hz, 1H), 6.44 (d, J = 16 Hz, 1H), 3.49 (d, J = 1 Hz, 3H) | 133 (M − $CF_3$) |
| Me | Cl | Cl | Chromatography on silica column | 58 | (400 MHz; DMSO-$d_6$) δ 13.04 (s, 1H), 7.08 (d, J = 15 Hz, 1H), 6.17 | 133 (M − Cl) |

TABLE 1-continued

| R³ | R⁴ | R⁵ | Purification of (VI) | Yield % for step (V) to (VI) | ¹H NMR of (I) | MS |
|---|---|---|---|---|---|---|
| CF₃ | Cl | F | Chromatography on silica column | 91 | (d, J = 15 Hz, 1H), 2.33 (s, 3H) (400 MHz; DMSO-d₆) δ 13.49 (s, 1H), 6.99 (dd, J = 18 Hz, 16 Hz, 1H), 6.55 (d, J = 16 Hz, 1H) | 171 (M − Cl) |
| CHF₂ | F | F | Filtration through silica | 80 | (300 MHz); DMSO-d6) δ 13.2 (s, 1H), 6.82 (dt, J = 16 Hz, 12 Hz, 1H), 6.64 (tt, J = 52 Hz, 4 Hz, 1H), 6.48 (dt, J = 16 Hz, 2 Hz, 1H) | |

The compounds (VI) of Table 1 were subsequently reacted as in Step D of Examples 1-3 above to produce the analogous enoic acid compounds (I).

Example 5

Synthesis of (E)-4,4-difluoropent-2-enoic acid

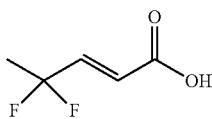

Step A: Ethyl 4,4-difluoro-3-oxo-pentanoate

Sodium hydride (14.5 g, 0.36 mol), toluene (120 ml) and ethyl acetate (2.9 ml, 0.029 mol) were combined under an atmosphere of nitrogen and heated to 50° C. Ethanol (1.7 ml, 0.03 mol) was added dropwise and the resulting slurry was stirred for 5 min. A mixture of ethyl 2,2-difluoropropanoate (40 g, 0.29 mol) and ethyl acetate (31.4 ml, 0.32 mol) was charged over 90 min with stirring keeping the temperature between 50 and 55° C. Stirring was continued for one hour after completion of addition. The mixture was allowed to reach room temperature and quenched by the parallel addition of aqueous sodium bicarbonate (0.72 M, 80 ml) and HCl (conc., ca. 20 ml) keeping the pH between 7.5 and 9.5. The resulting mixture was carried to Step B.

Step B: Ethyl 4,4-difluoro-3-hydroxy-pentanoate

The pH of the mixture from Step A was adjusted to 7.5 to 8.5 with conc. HCl. Subsequently, sodium borohydride (3.29 g, 0.087 mol) was added in portions while keeping the temperature between 15 and 25° C. and the pH below 9.5. After completion of addition the mixture was stirred for 1 hour. The pH was adjusted to 4-5 by the addition of conc. HCl and the layers were separated. The organic layer was washed with a solution of 1 g sodium bicarbonate in brine (50 ml), filtered through a short plug of magnesium sulfate, concentrated under reduced pressure to a volume of ca. 150 ml and carried to Step C.

Step C: Ethyl (E)-4,4-difluoropent-2-enoate

The residue of Step B was diluted with toluene (300 ml) and cooled to 0° C.

Methanesulfonylchloride (20.8 ml, 0.267 mol) was added followed by charging of triethylamine (39.1 ml, 0.28 mol) over 90 min while keeping the temperature below 10° C. Toluene (100 ml) was charged followed by triethylamine (50 ml, 0.357 mol) and the mixture was stirred overnight at room temperature. Water (100 ml) was added, the mixture was stirred until precipitates dissolved, the phases were separated and the organic phase was carried to Step D.

Step D: (E)-4,4-difluoropent-2-enoic acid

Water (40 ml) was charged to the residue of Step C and the mixture was stirred at 40 to 45° C. Aqueous NaOH (37 ml, 30%) was charged over 90 min keeping the temperature between 40 and 45° C. Stirring was continued for 90 min at this temperature, then heating was turned off and stirring was continued at room temperature for 72 hours. The phases were separated, the organic was phase back-extracted with water. From the combined aqueous phases ca. 20 ml were distilled off under reduced pressure. EtOH (15 ml) was added, the mixture was stirred at 0 to 10° C., the pH was adjusted to 2.5 to 3 with conc. HCl and the mixture was stirred for 30 min at this temperature. The pH was adjusted to 1.3 to 1.6 with conc. HCl, and the mixture was stirred at −4 to −10° C. for one hour. The precipitate was isolated by filtration, washed with water/EtOH (precooled, 80:20, 2×30 ml) and dried under reduced pressure to give 22.2 g of a solid (yield 56% for Steps A-D combined).

¹H-NMR (300 MHz; DMSO-d6) δ 12.99 (s, 1H), 6.83 (dt, J=16 Hz, 11 Hz, 1H), 6.23 (dt, J=16 Hz, 3 Hz, 1H), 1.79 (t, J=19 Hz, 3H), MS 271.0 (2M-H)

The invention claimed is:
1. A process to prepare a compound of Formula (I)

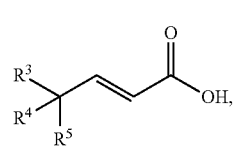

Formula (I)

wherein R³, R⁴ and R⁵ are each selected independently from hydrogen, halogen, alkyl, alkenyl, alkynyl, alkoxyl, and wherein the alkyl, alkenyl, alkynyl, and alkoxyl may be optionally substituted with one or more halogen, alkyl, alkenyl, alkynyl, and alkoxyl;
comprising
reacting a compound of Formula (II)

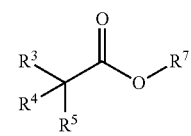

Formula (II)

wherein $R^3$, $R^4$ and $R^5$ are defined as above and $R^7$ is alkyl;
with a compound of Formula (III)

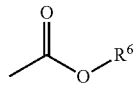
Formula (III)

wherein $R^6$ is alkyl,
and a base to form a compound of Formula (IV)

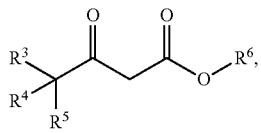
Formula (IV)

wherein $R^3$, $R^4$, $R^5$ and $R^6$ are defined as above; and
ii) reducing the compound of Formula (IV) with a reducing agent to form a compound of Formula (V)

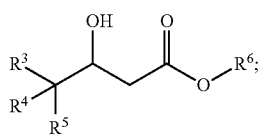
Formula (V)

a) reacting a compound of Formula (V)
wherein $R^3$, $R^4$, $R^5$ and $R^6$ are defined as above;
with methane sulfonyl chloride and a base to form a compound of Formula (VI)

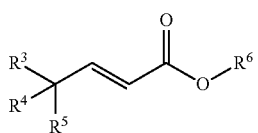
Formula (VI)

wherein $R^3$, $R^4$, $R^5$ and $R^6$ are defined as above; and
b) reacting a compound of Formula (VI) with a reagent to form a compound of Formula (I); and
wherein the steps i), ii), a) and b) are conducted without isolation of the intermediate compounds of Formulas IV, V or VI.

2. The process of claim 1, wherein the base of step i) is LiHMDS, sodium hydride, LDA, KOtBu or NaOEt.

3. The process of claim 1, wherein the reducing agent of step ii) is lithium borohydride, sodium borohydride, disiamylborane, hydrogen with platinum (IV) oxide, hydrogen with palladium/carbon or zinc borohydride.

4. The process of claim 1, wherein the base of step a) is an amine.

5. The process of claim 4, wherein the amine is triethylamine.

6. The process of claim 1, wherein the reagent of step b) is an acid or a base.

7. The process of claim 6, wherein the base is sodium hydroxide, lithium hydroxide or potassium hydroxide.

8. The process of claim 1, wherein at least one of $R^3$, $R^4$ and $R^5$ is halogen.

9. The process of claim 8, wherein the halogen is bromine, chlorine or fluorine.

10. The process of claim 1, wherein at least one of $R^3$, $R^4$ and $R^5$ is alkyl.

11. The process of claim 1, wherein $R^3$ is $CH_3$ and $R^4$ and $R^5$ are both fluorine.

12. The process of claim 1, wherein $R^6$ is ethyl.

13. The process of claim 1, wherein $R^7$ is methyl or ethyl.

14. The process of claim 1, wherein $R^3$ is Cl and $R^4$ and $R^5$ are both fluorine.

15. The process of claim 1, wherein $R^3$ is Br and $R^4$ and $R^5$ are both fluorine.

16. The process of claim 1, wherein $R^3$ is $CF_3$, $R^4$ is $CH_3O$ and $R^5$ is fluorine.

17. The process of claim 1, wherein $R^3$ is $CH_3$ and $R^4$ and $R^5$ are both chlorine.

18. The process of claim 1, wherein $R^3$ is $CF_3$, $R^4$ is chlorine and $R^5$ is fluorine.

* * * * *